| United States Patent [19] | [11] | 4,101,450 |
|---|---|---|
| Hwang et al. | [45] | Jul. 18, 1978 |

[54] CATALYST FOR PRODUCTION OF ACETIC ACID

[75] Inventors: H. Shinn Hwang, Livingston; Paul D. Taylor, Clinton, both of N.J.

[73] Assignee: Celanese Corporation, New York, N.Y.

[21] Appl. No.: 795,260

[22] Filed: May 9, 1977

[51] Int. Cl.$^2$ .................. B01J 29/12; B01J 29/22; B01J 23/40
[52] U.S. Cl. .................................. 252/460; 252/472; 260/541
[58] Field of Search ............................. 252/460, 472

[56] References Cited

U.S. PATENT DOCUMENTS

| 2,083,824 | 6/1937 | Bond et al. ................ 252/460 X |
| 2,880,241 | 3/1959 | Hughes et al. ............. 252/472 X |
| 3,055,840 | 9/1962 | Koch, Jr. ................... 252/460 X |
| 3,176,038 | 3/1965 | Zachry et al. .............. 252/460 X |
| 3,318,913 | 5/1967 | Falbe et al. ................ 252/472 X |
| 3,909,456 | 9/1975 | Numagami et al. ........... 252/472 |

*Primary Examiner*—Carl F. Dees

[57] ABSTRACT

This invention provides a novel rhodium-ruthenium catalyst composition which is adapted for highly selective conversion of synthesis gas to acetic acid and related oxygenated two-carbon hydrocarbon derivatives.

5 Claims, No Drawings

CATALYST FOR PRODUCTION OF ACETIC ACID

BACKGROUND OF THE INVENTION

The production of hydrocarbons and oxygenated hydrocarbon derivatives from synthesis gas (i.e., carbon monoxide/hydrogen) is a developing technology, and it is increasingly being introduced into commercial applications. Reaction conditions for synthesis gas conversion generally involve temperatures in the range of about 150–500° C, pressures in the range of about 15–10,000 psi, carbon monoxide/hydrogen molar ratios in the range of about 10:1 to 1:10, and hydrogenation catalysts selected from Group VIII metals.

The technical literature on synthesis gas conversion is extensive. Illustrative of prior art publications are U.S. Pat. Nos. 2,681,924; 2,686,195; 2,686,801; 2,696,506; 2,729,664; 2,753,367; 2,767,202; 2,770,635; 2,786,863; 2,957,902; and the references cited therein.

Efforts to convert synthesis gas into a definitive class of products has not been readily accomplished. Most synthesis gas conversion processes yield a broad molecular weight distribution of products, which range from methane to polymeric derivatives.

In German Offen. No. 2,503,233 there is a detailed review of prior art literature relating to the use of rhodium metal as a synthesis gas conversion catalyst. Selective production of oxygenated two-carbon hydrocarbons from synthesis gas is a desirable objective, but prior art processes report only low yields of products such as acetic acid, ethanol, acetaldehyde and ethyl acetate.

German Offen. No. 2,503,233 describes an improved process for converted synthesis gas into oxygenated $C_2$-hydrocarbon derivatives in the presence of a rhodium metal catalyst. The preferred catalyst is 5% rhodium metal on a silica support.

There remains a need for improvements in catalysts and processes for efficient and highly selective conversion of synthesis gas into oxygenated $C_2$-hydrocarbon products.

Accordingly, it is an object of the present invention to provide a process for selective conversion of synthesis gas into oxygenated $C_2$-hydrocarbon products such as acetic acid, ethanol, acetaldehyde and ethyl acetate.

It is another object of this invention to provide an improved process for converting synthesis gas into acetic acid with an efficiency of at least about 30 weight percent.

It is another object of this invention to provide an improved rhodium catalyst which is highly reactive and highly selective for conversion of synthesis gas into oxygenated $C_2$-hydrocarbon products.

It is a further object of this invention to provide a method for preparing and pretreating a hydrogenation catalyst adapted for selective conversion of synthesis gas into acetic acid.

Other objects and advantages of the present invention shall become apparent from the accompanying description and examples.

DESCRIPTION OF THE INVENTION

One or more objects of the present invention are accomplished by the provision of a process for selective conversion of synthesis gas into oxygenated $C_2$-hydrocarbon derivatives which comprises continuously passing a carbon monoxide/hydrogen feed stream in contact with a rhodium-ruthenium catalyst composition in a reaction zone maintained at a temperature between about 150° C and 500° C and a pressure between about 100 and 10,000 psi.

One or more other objects of the present invention are accomplished by the provision of a method for the preparation and pretreatment of a catalyst composition which is highly selective for the production of oxygenated $C_2$-hydrocarbon derivatives from synthesis gas which comprises (1) co-impregnating a carrier substrate with an aqueous solution of soluble rhodium and ruthenium compounds, and subjecting the co-impregnated carrier substrate to drying conditions to remove substantially all of the water content, wherein the resultant catalyst composition consists essentially of between about 0.1 and 10 weight percent rhodium metal and between about 0.01 and 2 weight percent ruthenium metal, based on the total catalyst composition weight; (2) calcining and reducing the catalyst composition by contacting said catalyst composition with hydrogen at a temperature between about 200° C and 500° C; and (3) subsequently heating the catalyst composition in a static atmosphere of carbon monoxide and hydrogen at a temperature between about 150° C and 350° C for a time period between about 0.2 and 20 hours.

By the term "static" atmosphere of carbon monoxide and hydrogen in step (3) of the catalyst preparation method is meant a closed system of carbon monoxide and hydrogen which is maintained in equilibrious contact with the catalyst composition. The static atmospheric treatment of the catalyst is completed before the continuous passing of a carbon monoxide/hydrogen feed stream through the catalyst contacting zone is commenced.

Catalyst Preparation

Several important aspects of catalyst preparation and pretreatment must be respected in order to achieve a present invention rhodium-ruthenium catalyst composition which exhibits high reactivity and high selectivity for synthesis gas conversion into acetic and other related oxygenated $C_2$-hydrocarbon derivatives such as ethanol, acetaldehyde and ethyl acetate.

The rhodium-ruthenium bimetallic alloy component of the present invention catalyst must be supported on a carrier substrate. The respective quantities of metals in a catalyst composition must consist essentially of between about 0.1 and 10 weight percent rhodium metal, and between about 0.01 and 2 weight percent ruthenium metal, based on the total catalyst composition weight. Preferably, the metal content of a catalyst composition is in the range between 1 and 5 weight percent rhodium metal, and between about 0.1 and 1 percent ruthenium metal, based on the total catalyst composition weight.

The carrier substrate is preferably a high surface area particulated material of the type conventionally employed in the preparation of heterogeneous catalyst systems. The substrate material nominally has a surface area of at least about one square meter per gram. Silica gel is a highly preferred carrier substrate material for the preparation of the present invention rhodium-ruthenium catalyst compositions. Illustrative of other suitable carrier substrate materials are alpha-alumina, gamma-alumina, eta-alumina, silica-alumina, magnesia, carbon, zeolites, and the like.

In a preferred method of catalyst preparation, an aqueous solution of appropriate quantities of selected water-soluble rhodium and ruthenium compounds is employed to co-impregnate high surface area carrier substrate material with the respective metal compounds. Illustrative of water-soluble compounds are the chloride and nitrate salts of rhodium and ruthenium.

The co-impregnated carrier substrate material is subjected to drying conditions to lower the water content of the resultant catalyst composition to the lowest possible level. In a typical drying procedure, the catalyst composition is slowly heated in an oxygen-free atmosphere up to a temperature of about 75°–150° C, and the drying is continued for a period of time between about 0.5–24 hours until substantially all of the water content of the catalyst composition is removed.

As a further required step in the procedure for catalyst production, the dry-state catalyst composition is reduced with hydrogen to form a metal alloy of rhodium and ruthenium on the carrier substrate. It has been found advantageous to conduct the reduction of catalyst rhodium and ruthenium compounds to the free metal state by contacting the catalyst composition with hydrogen, and then heating the catalyst reduction zone slowly from room temperature up to about 500° C over a period between about 1–3 hours. It is highly preferred that the catalyst reduction zone is maintained at the elevated temperature limit for an additional 0.5–5 hours in order to insure complete reduction of metal compounds into free metal alloy components.

If a rhodium-ruthenium catalyst composition prepared and reduced as described above is charged to a synthesis gas conversion zone, then the selective yield of desirable oxygenated $C_2$-hydrocarbon derivatives obtained is not optimal. Further, in a given series of synthesis gas runs, the reactivity and stability of the rhodium-ruthenium catalyst is variable, and the high selectivity conversion of synthesis gas to oxygenated $C_2$-hydrocarbon derivatives is inconsistent in yield and relative product distribution.

Accordingly, it is an important requirement of the present invention method of catalyst preparation that the rhodium-ruthenium catalyst composition obtained from the above-described procedure for catalyst construction and reduction is subjected to a pretreatment step, prior to the application of the said catalyst for selective synthesis gas conversion to oxygenated $C_2$-hydrocarbon products.

Such pretreatment procedure involves heating the calcined and reduced catalyst composition in a static atmosphere of carbon monoxide and hydrogen at a temperature between about 150° C and 350° C for a pretreatment period between about 0.2 and 20 hours.

The molar ratio of carbon monoxide to hydrogen in the static atmosphere can be in the range between about 0.5 and 10 to 1, and the pressure can be in the range between about 50 and 5000 psi.

If a catalyst composition is calcined and reduced, and not subsequently pretreated with a static atmosphere of carbon monoxide and hydrogen, then the said catalyst composition rapidly deactivates when employed for synthesis gas conversion. Hence, it was observed that a rhodium-ruthenium catalyst which was prepared in accordance with the present invention except for the above-described pretreatment with a static atmosphere of carbon monoxide and hydrogen, converted synthesis gas at the rate of 5.3 g/l/hr. to a liquid product mixture containing 91.5 weight percent water and 7 weight percent oxygenated $C_2$-hydrocarbon products.

Under comparable conditions a present invention rhodium-ruthenium catalyst composition which was calcined and reduced, and then heated at 220° C in a static atmosphere of carbon monoxide/hydrogen (3:1) at a pressure of 810 psi, converted synthesis gas at the rate of 22 g/l/hr. to a liquid product mixture containing 47.8 weight percent water and 49 weight percent oxygenated $C_2$-hydrocarbon products.

Synthesis Gas Conversion

In another embodiment, this invention provides an improved process for selective conversion of synthesis gas into acetic acid and related oxygenated $C_2$-hydrocarbon derivatives such as ethanol, acetaldehyde and ethyl acetate. The improved process involves continuous passage of a carbon monoxide/hydrogen stream under synthesis gas conversion conditions in contact with a present invention rhodium-ruthenium catalyst composition which has been prepared and pretreated in the manner described hereinabove.

The synthesis gas conversion zone is preferably a high pressure and high temperature gradientless reactor system in which the catalyst composition is confined within the dimensions of a flow-through basket-like container.

The molar ratio of carbon monoxide to hydrogen in the synthesis gas feed stream can vary in the range between about 1 and 20 to 1. It is highly preferred that the molar ratio of carbon monoxide to hydrogen be maintained in the range between about 1.5 and 10 to 1 for optimal conversion of synthesis gas to acetic acid.

The synthesis gas conversion temperature can vary in the range between about 150° C and 500° C, and preferably is maintained in the range between about 200° C and 350° C.

The synthesis gas conversion pressure can vary in the range between about 100 and 10,000 psi, and preferably is maintained in the range between about 500 and 3000 psi.

The synthesis gas conversion is preferably conducted under reaction conditions of feed gas composition, temperature, pressure space velocity, and the like, so as to convert the synthesis gas selectively into a liquid product mixture which contains at least 30 weight percent acetic acid. Under optimum synthesis gas conversion conditions, the production of methane, methanol and three-carbon or higher hydrocarbon derivatives is minimized.

Higher temperatures tend to increase total synthesis gas conversion, but concomitantly larger quantities of methane and water are produced. Because of the highly exothermic nature of synthesis gas conversion, the temperature of the reaction zone must be controlled in order to prevent a runaway methanation effect.

The space velocity of the synthesis gas feed stream is generally maintained in the range of about $10^3$ and $10^6$ hourly space velocity (i.e., volumes of synthesis gas, at 0° C and 1 atmosphere, per volume of catalyst per hour).

Conventional methods of collecting gaseous and liquid efficient product streams can be employed.

The following examples are illustrative of specific embodiments of the present invention catalyst preparation and synthesis gas conversion. In the light of the foregoing disclosure numerous modifications are possible in the practice of the present invention without departing from the scope thereof.

EXAMPLE I

This Example illustrates the preparation of a nominal 5% rhodium on silica catalyst in accordance with German Offen. No. 2,503,233.

A 3.34 gram quantity of rhodium chloride (Englehard, 41.8% Rh) was dissolved in water. The resultant aqueous solution was employed to impregnate 30.6 grams of silica gel (Davison Grade 57).

The impregnated silica gel composition was dried under nitrogen at 80° C for 1 hour, at 110° C for one hour, and then at 120° C overnight.

EXAMPLE II

This Example illustrates the pretreatment of a prior art catalyst, and its use for the conversion of synthesis gas into oxygenated $C_2$-hydrocarbons and other derivatives.

A quantity of a 5% rhodium on silica catalyst prepared in the manner described in Example I was reduced by contact with hydrogen at 450° C for 2 hours. The reduced catalyst was charged to the catalyst basket of a high pressure-high temperature continuous flow gradientless reactor system. The reactor was purged with nitrogen, and with a carbon monoxide/hydrogen (1:1) stream.

The reactor was then slowly heated to 220° C, while the catalyst was maintained in contact with a closed system of carbon monoxide/hydrogen (1:1) at 850 psi.

When the reactor temperature had reached 220° C, the carbon monoxide/hydrogen (1:1) feed stream was passed continuously from a high pressure vessel through a metering valve to the reactor. A gasiform product mixture was continuously withdrawn from the reactor system, and all liquid components of the product mixture were condensed and collected. The uncondensable gasiform material was vented from the system.

The synthesis gas conversion was conducted in two runs of 2-4 hours in duration. The composition of liquid product mixtures was analyzed by gas chromatography.

The reaction conditions and product composition data are summarized as Run Numbers 1-2 in Table I for comparison with data obtained with the novel rhodium-ruthenium catalyst compositions of the present invention.

EXAMPLE III

This Example illustrates the preparation and pretreatment of a rhodium-ruthenium catalyst composition in accordance with the present invention, and its use for the conversion of synthesis gas into acetic acid and related oxygenated $C_2$-hydrocarbons.

A solution was prepared by dissolving 2.967 grams of rhodium chloride and 0.646 grams of ruthenium chloride in 87.4 milliliters of water. A 72.8 gram quantity of silica gel (Davison Grade 57) was co-impregnated with the aqueous solution of rhodium and ruthenium salts.

The co-impregnated silica gel composition was dried under nitrogen at 80° C for 1 hour, and then at 120° C overnight.

The resultant catalyst composition was reduced by contact with hydrogen under a slowly increasing temperature gradient from room temperature to 450° C. The reduction conditions were maintained at a temperature of 450° C for 2 hours.

The catalyst thus prepared nominally contained 2 weight percent rhodium metal and 0.44 weight percent ruthenium metal, based on the total catalyst composition weight.

In the manner described in Example II, the reduced catalyst was charged to the catalyst basket of a gradientless reactor system. The reactor was purged with nitrogen, and then with carbon monoxide/hydrogen (3:1).

The reactor was slowly heated to 242° C, while the catalyst was maintained in contact with a static atmosphere of carbon monoxide/hydrogen (3:1) at 1425 psi for 2 hours.

At a temperature of 242° C, a carbon monoxide/hydrogen (3:1) feed stream was passed continuously through the catalyst zone, a product mixture was continuously withdrawn, and the liquid constituents of the product mixture were condensed and collected. The liquid condensate product mixture was analyzed by gas chromatography.

The above-described synthesis gas conversion run was conducted for a period of 2-4 hours. A second run was conducted for 2-4 hours under slightly different reaction conditions. The reaction conditions and product composition data of the two runs are summarized as Run Numbers 3-4 in Table I.

The data presented in Run Numbers 1-4 in Table I provide evidence that a rhodium-ruthenium catalyst composition in accordance with the present invention has a higher reactivity and higher selectivity than a prior art rhodium catalyst for the conversion of synthesis gas to acetic acid and other related oxygenated $C_2$-hydrocarbon derivatives.

It is to be noted that in Run Numbers 3-4 the conversion efficiency of synthesis gas to acetic acid was 33.4 and 32.2 weight percent, respectively. The corresponding conversion efficiency for the prior art rhodium catalyst in Run Numbers 1-2 was 7.3 and 8.1 weight percent, respectively. Also, the total yield of oxygenated $C_2$-hydrocarbon products was higher for the present invention Run Numbers 3-4 than for the prior art Run Numbers 1-2.

EXAMPLE IV

This Example illustrates the higher selectivity of invention rhodium-ruthenium catalyst compositions in comparison with a prior art rhodium catalyst composition for synthesis gas conversion in terms of total yield of oxygenated $C_2$-hydrocarbon derivatives.

A prior art 2.5% rhodium on silica catalyst was prepared in the manner described in Examples I-II above.

A 1.5% rhodium-1% ruthenium on silica catalyst and a 1% rhodium-1.5% ruthenium on silica catalyst were prepared in accordance with the present invention procedure described in Example III above.

Table II is a summary of synthesis gas conversion runs conducted with the 2.5% rhodium on silica catalyst of the prior art and the two present invention rhodium-ruthenium catalysts for comparison purposes.

The synthesis gas (3:1) conversion with each catalyst was conducted at a temperature of 252° C and a pressure of 1400 psi.

As reported in Table II, the prior art Run Number 1 produced a conversion efficiency yield of 27.5 weight percent of oxygenated $C_2$-hydrocarbon products. In the present invention Run Numbers 2-3, the total yield of oxygenated $C_2$-hydrocarbon products was 39.6 and 46.6 weight percent, respectively.

TABLE I

| Run No. | Catalyst | Reaction Conditions | | | Liq. g/l/hr. | Selectivity, wt.% | | | | | | $C_2^{(1)}$ Total |
|---|---|---|---|---|---|---|---|---|---|---|---|---|
| | | T,°C | P,psi | CO/H$_2$ | | H$_2$O | MeOH | AcH | EtOH | HOAc | EtAc | |
| 1 | 5% Rh/SiO$_2$ | 220 | 850 | 1 | 41 | 53.8 | 1.3 | 2.9 | 26.4 | 7.3 | 5.0 | 41.6 |
| 2 | " | 228 | 1430 | 1 | 31 | 44.6 | 2.1 | 1.6 | 29.4 | 8.1 | 8.7 | 47.8 |
| 3 | Rh-Ru/SiO$_2$ (2% Rh, 0.44% Ru) | 242 | 1425 | 3 | 44 | 46.4 | — | 7.7 | — | 33.4 | 12.0 | 53.1 |
| 4 | " | 234 | 810 | 3 | 43 | 38.1 | 0.2 | 5.1 | 8.8 | 32.2 | 12.0 | 58.1 |

$^{(1)}$C$_2$ includes acetaldehyde, ethanol, acetic acid and ethyl acetate.

TABLE II

| Run No. | Catalyst | Conversion | | STY g/l/hr. | Selectivity, wt.% | | | | | | $C_2^{(1)}$ Total |
|---|---|---|---|---|---|---|---|---|---|---|---|
| | | H$_2$ | CO | | H$_2$O | MeOH | AcH | EtOH | HOAc | EtAc | |
| 1 | 2.5% Rh | 35.6 | 5.2 | 37.3 | 68.8 | 0.7 | 2.2 | 10.2 | 13.3 | 1.8 | 27.5 |
| 2 | 1.5% Rh–1% Ru | 41.5 | 9.4 | 37.3 | 54.8 | 1.9 | 2.4 | 22.0 | 10.6 | 4.6 | 39.6 |
| 3 | 1% Rh–1.5% Ru | 38.5 | 11.2 | 32.8 | 42.7 | 0.7 | 2.6 | 18.3 | 16.6 | 9.1 | 46.6 |

$^{(1)}$C$_2$ includes acetaldehyde, ethanol, acetic acid and ethyl acetate.

What is claimed is:

1. A method for the preparation and pretreatment of a catalyst composition which is highly selective for the production of oxygenated C$_2$-hydrocarbon derivatives from synthesis gas which comprises (1) co-impregnating a carrier substrate with an aqueous solution of soluble rhodium and ruthenium compounds, and subjecting the co-impregnated carrier substrate to drying conditions to remove substantially all of the water content, wherein the resultant catalyst composition consists essentially of between about 0.1 and 10 weight percent rhodium metal and between about 0.01 and 2 weight percent ruthenium metal, based on the total catalyst composition weight; (2) calcining and reducing the catalyst composition by contacting said catalyst composition with hydrogen at a temperature between about 200° C and 500° C; and (3) subsequently heating the catalyst composition in a static atmosphere of carbon monoxide and hydrogen at a temperature between about 150° C and 350° C for a time period between about 0.2 and 20 hours.

2. A method in accordance with claim 1 wherein the step (2) calcining and reducing procedure is conducted for a time period between about 0.5 and 3.0 hours.

3. A method in accordance with claim 1 wherein the molar ratio of carbon monoxide to hydrogen in the static atmosphere in step (3) is in the range between about 0.5 and 10, and the pressure of the static atmosphere is between about 50 and 5000 psi.

4. A rhodium-ruthenium catalyst composition prepared and pretreated in accordance with the method of claim 1.

5. A rhodium-ruthenium catalyst composition in accordance with claim 4 wherein the carrier substrate is silica gel.

* * * * *